United States Patent [19]

Sarpeshkar et al.

[11] Patent Number: 5,177,170

[45] Date of Patent: Jan. 5, 1993

[54] RADIOPAQUE POLYURETHANES

[75] Inventors: Ashok M. Sarpeshkar, Upper Saint Clair; Peter H. Markusch, Pittsburgh, both of Pa.

[73] Assignee: Miles Inc., Pittsburgh, Pa.

[21] Appl. No.: 907,882

[22] Filed: Jul. 2, 1992

[51] Int. Cl.⁵ .................... C08G 18/30; C08G 18/32
[52] U.S. Cl. ...................................... 528/76; 528/77; 528/85
[58] Field of Search ........................... 528/76, 77, 85

[56] References Cited

U.S. PATENT DOCUMENTS

| | | | |
|---|---|---|---|
| 2,212,334 | 8/1940 | Wallerich | 18/58 |
| 2,857,915 | 10/1958 | Sheridan | 128/349 |
| 3,529,633 | 9/1970 | Vaillancourt | 138/118 |
| 3,605,555 | 9/1971 | Wise | 91/50 |
| 3,605,750 | 9/1971 | Sheridan et al. | 128/348 |
| 3,618,614 | 11/1971 | Flynn | 128/348 |
| 3,645,955 | 2/1972 | Flynn | 260/31.4 |
| 3,749,134 | 7/1973 | Slingluff et al. | 138/177 |
| 3,901,829 | 8/1975 | Slingluff et al. | 252/478 |
| 4,027,659 | 6/1977 | Slingluff | 128/2 M |
| 4,105,732 | 8/1978 | Slingluff | 264/104 |
| 4,182,787 | 1/1980 | Goossens et al. | 428/36 |
| 4,722,344 | 2/1988 | Cambron et al. | 128/658 |
| 5,045,624 | 9/1991 | Falk et al. | 528/70 |

OTHER PUBLICATIONS

Y. Delaviz et al., Polymer Preprints (Polymer Division, Am. Chem. Soc.), 30, 215–216 (1989).

*Primary Examiner*—Morton Foelak
*Attorney, Agent, or Firm*—Joseph C. Gil; Richard E. L. Henderson

[57] ABSTRACT

This invention relates to radiopaque polyurethane compositions which are reaction products of
(a) cycloaliphatic diisocyanates;
(b) at least one polyether diol having a molecular weight of from about 500 to about 6000; and
(c) an isocyanate-reactive bromine-containing compound selected from the group consisting of
  (i) tetrabromodipentaerythritol and
  (ii) a mixture of tetrabromodipentaerythritol and dibromoneopentyl glycol; and
(d) optionally, a catalyst;
wherein the amount of component (c) is such that bromine constitutes at least 15% by weight of the polyurethane composition, wherein the weight ratio of component (b) to component (c) is from about 2:98 to about 55:45, and wherein the components are reacted at an isocyanate index of from about 95 to about 120.

5 Claims, No Drawings

RADIOPAQUE POLYURETHANES

BACKGROUND OF THE INVENTION

This invention relates to radiopaque polyurethane compositions having a bromine content of at least 15% by weight prepared by the reaction of cycloaliphatic diisocyanates, certain polyether diols, and a sufficient amount of tetrabromodipentaerythritol or a mixture thereof with dibromoneopentyl glycol to provide the required bromine content.

When medical or veterinary devices are inserted or implanted in a subject, it is often desirable to be able to locate them by X-ray examination, particularly when catheters or cannulas are being inserted into body cavities, passages, or vessels. It is also often desirable, especially with catheters, to observe visually fluids within exposed portions of such devices.

Consequently, an object of the present invention is to prepare radiopaque polyurethane compositions that are optically transparent.

Several approaches for achieving this object in catheters have been reported. For example, U.S. Pat. No. 2,212,334 discloses the incorporation of short segments of radiopaque material within otherwise transparent tubes by introduction of such material at regular intervals during manufacture of the catheters. Alternatively, U.S. Pat. Nos. 2,857,915, 4,027,659, and 4,105,732 disclose the introduction of the radiopaque material as continuous stripes running the length of the catheters. It is also possible to include a radiopaque material only at the distal end of the catheter, as disclosed in U.S. Pat. No. 3,605,750, but the intervening portion of the catheter is not readily detectable by X-ray examination. Similarly, U.S. Pat. No. 3,529,633 discloses catheters made primarily from polymers that are opaque to both X-rays and visible light but also have small sections made from transparent materials.

Another variant of this approach is described in U.S. Pat. No. 3,618,614, which discloses a multiwall tubing having a thick transparent inner tube encased within a thin transparent tube containing a radiopaque material. In this variant, the relatively longer pathlength through edges of the tube provides sufficient contrast to appear during X-ray examination. U.S. Pat. No. 3,336,918 discloses similar effects obtained by incorporating metal powders into polyurethane coatings.

Yet another approach is to disperse X-ray opaque substances, such as barium sulfate, a bismuth halide, or a halogen-containing plasticizer, diol, or other such halogen-containing material, throughout a visually transparent polymer. See, for example, Y. Delaviz et al., *Polymer Preprints* (Polymer Division, Am. Chem. Soc.), 30, 215-216 (1989), and U.S. Pat. Nos. 3,608,555, 3,645,955, 3,749,134, 3,901,829, and 4,282,876. Blends of polymers, at least one of which is radiopaque, are reported, for example, in U.S. Pat. No. 4,182,787, to provide similar effects. Each of these approaches, however, involves the use of physical blends, at least some of which have inherent disadvantages. For example, some of the radiopaque substances can be leached out of the polymeric substrate and absorbed by the body. In addition, some additives can have other incompatibilities that make them unsuitable for use in humans or animals.

It would be particularly advantageous to make the medical or veterinary devices from a polymeric material in which the radiopaque component is incorporated as a structural unit of the polymer. For example, U.S. Pat. No. 4,722,344, which is incorporated by reference, discloses polyurethanes prepared using halogenated polyols and/or halogenated polyisocyanates as reactants. Although the polyurethanes disclosed in U.S. Pat. No. 4,722,344 incorporate sufficient bromine to provide the desired radiopacity, these polyurethanes have a high flex modulus and are not as soft as desired under saline conditions (such as typical of blood). For example, when using a chain extender such as dibromoneopentyl glycol, the desired bromine content (about 25% of the weight of polyurethane) can be achieved only by using a relatively large quantity of the chain extender, which results in a comparatively large hard segment content (i.e., the sum of the amounts of the low molecular weight chain extender and polyisocyanate components) relative to the soft segment content (i.e., the amount of the higher molecular weight polyol component). During use, such relatively hard polyurethanes could irritate tissues with which they are in contact. In addition, even slightly rough surfaces could increase the possibility of transporting bacteria into the body, particularly skin bacteria contacted at the point of entry into the body. The polyurethane can be softened by known methods, for example, by introducing hydrophilic structural units such as non-ionic groups (e.g., polyoxyethylene groups) or ionic groups, but such methods would undesirably reduce the bromine content and could adversely affect various physical properties of the polyurethane.

It was, therefore, an object of the present invention to obtain optically transparent radiopaque polyurethanes that have high halogen content but which are soft, especially under physiological conditions. This object has been accomplished by partially or completely replacing the previously reported brominated chain extenders with tetrabromodipentaerythritol.

SUMMARY OF THE INVENTION

This invention relates to a radiopaque polyurethane composition comprising a reaction product of
(a) a cycloaliphatic diisocyanate;
(b) at least one polyether diol having a molecular weight of from about 500 to about 6000;
(c) an isocyanate-reactive bromine-containing compound selected from the group consisting of
  (i) tetrabromodipentaerythritol and
  (ii) a mixture of tetrabromodipentaerythritol and dibromoneopentyl glycol; and
optionally, a catalyst;
wherein the amount of component (c) is such that the amount of bromine in the polyurethane composition is at least 15% by weight (preferably 20 to 30% by weight),
wherein the weight ratio of component (b) to component (c) is from about 2:98 to about 55:45 (preferably from 10:90 to 60), and
wherein the components are reacted at an isocyanate index of from about 0.95 to about 1.2.

DETAILED DESCRIPTION OF THE INVENTION

Suitable diisocyanates for preparing the polyurethane compositions of the invention are those containing one or more cycloaliphatic hydrocarbon groups containing 4 to about 15 (preferably 5 to 10) carbon atoms. Examples of suitable such cycloaliphatic diisocyanates include cyclobutane-1,3-diisocyanate, cyclohexane-1,3- and -1,4-diisocyanate and mixtures thereof, 1-isocyanato-3,3,5-trimethyl-5-isocyanatomethylcyclohexane (isophorone diisocyanate), 2,4- and 2,6-hexahydrotoluene diisocyanate and mixtures thereof, hexahydro-1,3- and/or -1,4-phenylene diisocyanate, and dicyclohexylmethane-4,4'-diisocyanate ("hydrogenated MDI", or "HMDI"). Dicyclohexylmethane-4,4'-diisocyanate is particularly preferred.

Suitable polyether diols have a molecular weight of from about 500 to about 6000. Such compounds are known and may be prepared, for example, by the polymerization of epoxides, optionally in the presence of a catalyst such as $BF_3$, or by chemical addition of such epoxides, optionally as mixtures or successively, to starting components containing reactive hydrogen atoms. Suitable epoxides include ethylene oxide, propylene oxide, butylene oxide, tetrahydrofuran, styrene oxide, or epichlorohydrin. Suitable starter components include water, alcohols, or amines, including, for example, ethylene glycol, 1,3- or 1,2-propanediol, 1,2-, 1,3-, or 1,4-butanediol, trimethylolpropane, 4,4'-dihydroxydiphenylpropane, aniline, ammonia, ethanolamine, or ethylene diamine. Sucrose polyethers of the type described, for example, in German Auslegeschriften 1,176,358 and 1,064,938 may also be used according to the invention. Polyethers that contain predominantly primary hydroxyl groups (up to about 90% by weight, based on all of the hydroxyl groups in the polyether) are generally preferred. Polyethers modified by vinyl polymers of the kind obtained, for example, by the polymerization of styrene and acrylonitrile in the presence of polyethers (e.g., U.S. Pat. Nos. 3,383,351, 3,304,273, 3,523,093, and 3,110,695 and German Patentschrift 1,152,536) are also suitable, as are polybutadienes containing hydroxyl groups. Particularly preferred polyethers include polyoxyalkylene polyether polyols, such as polyoxyethylene diol, polyoxypropylene diol, polyoxybutylene diol, and polytetramethylene diol. Mixtures of such polyols are, of course, also suitable.

The chain extender tetrabromodipentaerythritol can be obtained commercially (for example, from Ameribrom, Inc.) or may be prepared by methods known in the art (for example, U.S. Pat. Nos. 3,864,306, 3,872,155, and 4,725,638). The optional brominated chain extender dibromoneopentyl glycol can also be obtained commercially (for example, from Ameribrom, Inc. or Great Lakes Chemical Corporation or may be prepared by methods known in the art (for example, U.S. Pat. No. 4,722,344). It is, of course, also possible, although not preferred, to use other brominated chain extenders known in the art in addition to or instead of dibromoneopentyl glycol.

The brominated chain extender is used in an amount such that the amount of bromine is sufficient to render the polyurethane radiopaque. The term "radiopaque" refers to the property of polyurethane compositions of the invention that allows articles prepared from such compositions to be detected by customary X-ray examination procedures after insertion into the patient. It has been found that a bromine content of at least 15% by weight (preferably 20 to 30% by weight) of polyurethane is generally sufficient. At the same time, the polyether diol component (b) and the brominated chain extender component (c) are used in quantities such that the weight ratio of the polyether diol to the brominated chain extender is from about 2:98 to about 55:45 (preferably from 10:90 to 40:60).

Suitable catalysts can be any of the catalysts normally used for the preparation of polyurethanes. Preferred catalysts include the organic metal compounds, especially organic tin compounds. Suitable organic tin compounds include those containing sulfur, such as dioctyl tin mercaptide (German Auslegeschrift 1,769,367 and U.S. Pat. No. 3,645,927), and, preferably, tin(II) salts of carboxylic acids, such as tin(II) acetate, tin(II) octoate, tin(II) ethylhexoate, and tin(II) laurate, as well as tin(IV) compounds, such as dibutyltin dilaurate.

Suitable but less preferred catalysts include tertiary amines such as triethylamine, tributylamine, N-methylmorpholine, N-ethylmorpholine, N,N,N',N'-tetramethylethylene diamine, pentamethyldiethylene triamine, and higher homologues (German Offenlegungsschriften 2,624,527 and 2,624,528), 1,4-diazabicyclo[2.2.2]octane, N-methyl-N'(dimethylaminoethyl)piperazine, bis(dimethylaminoalkyl)piperazines (German Offenlegungsschrift 2,636,787), N,N-dimethylbenzylamine, N,N-dimethylcyclohexylamine, N,N-diethylbenzylamine, bis(N,N-diethylaminoethyl) adipate, N,N,N',N'-tetramethyl-1,3-butanediamine, N,N-dimethyl-$\beta$-phenylethylamine, 1,2-dimethylimidazole, 2-methylimidazole, monocylic and bicyclic amidines (German Offenlegungsschrift 1,720,633), bis(dialkylamino)alkyl ethers (U.S. Pat. No. 3,330,782, German Auslegeschrift 030,558, and German Offenlegungsschriften 1,804,361 and 2,618,280), and tertiary amines containing amide groups (preferably formamide groups) according to German Offenlegungsschriften 2,523,633 and 2,732,292. The catalysts used may also be the known Mannich bases of secondary amines (such as dimethylamine) and aldehydes (preferably formaldehyde) or ketones (such as acetone) and phenols.

Any of the above-mentioned catalysts may, of course, be used as mixtures.

The catalysts can be premixed with the diisocyanate component, the polyether diol component, or, less preferably because of potential side reactions, the brominated chain extender, or they can be added separately.

The polyurethane compositions are prepared by any of several methods known in the art. The polyurethane-forming reaction components may be reacted by the known one-stage process, by the prepolymer process, or by the semiprepolymer process. Machines, such as those described in U.S. Pat. No. 2,764,565, may be used in many of these processes. Particulars of the processing machines which may also be used to produce polyurethanes according to the invention may be found in Kunststoff-Handbuch, Vol. VII, Vieweg and Höchtlen, Carl-Hanser-Verlag, Munich 1966, pages 121 to 205.

In the one-stage (or "one-shot") method, the isocyanate-reactive components, including the polyether diol and the isocyanate-reactive bromine-containing compound, as well as any additives and auxiliaries, are combined and thoroughly blended in a premix. The cycloaliphatic diisocyanate is then mixed with the premix. The isocyanate-reactive and diisocyanate components can be mixed batchwise or in a processing machine and poured into a mold or can be introduced separately into a mold where the polymerization reaction takes place. External release agents, such as silicone oils, are often used during the molding process. It is, however, also possible to use so-called "internal release agents", optionally in admixture with external release agents, as described, for example, in German Offenlegungsschriften 2,121,670 and 2,307,589.

In the prepolymer method, a prepolymer is formed by reacting the diisocyanate with a portion of the polyether diol or a blend of the polyether diol with the bromine-containing compound. The prepolymer is then allowed to react with the balance of the isocyanate-reactive components to form a polyurethane composition of the invention.

The semiprepolymer method is similar to the prepolymer method except that a portion of the cycloalkyl diisocyanate remains unreacted. That is, the isocyanate component is a mixture of unreacted diisocyanate and true prepolymer. As in the prepolymer method, the semiprepolymer is then allowed to react with the balance of the isocyanate-reactive components to form a polyurethane.

Regardless of the method used, the reactive components are used in quantities such that the isocyanate index is from about 0.95 to about 1.2 (preferably 0.95 to 1.1). By "isocyanate index" is meant the quotient of the number of isocyanate groups divided by the number of isocyanate-reactive groups.

The radiopaque thermoplastic polyurethanes of the invention may be processed by melt processing techniques known in the art. For example, slabs of the polyurethane can be chopped into strips and further granulated into smaller pieces. After being dried in a vacuum oven, the resultant ground material can be melt extruded on a single screw or twin screw extruder into strands that are then pelletized. In contrast to aromatic polyisocyanate-based thermoplastic polyurethanes that are melt extruded at temperatures of about 175° C. to 400° C., polyurethanes of the present invention can be successfully melt extruded at much lower temperatures, for example, as low as about 90° C. (preferably 90° C. to 200° C.). The pelletized material may then be subjected to a second melt processing step to produce the desired articles. Thus, the polyurethanes of the invention may be extruded into tubes and catheters of various internal and external diameters and gauges. Furthermore, they may be again extruded, co-extruded with other polymers, or injection molded into virtually any desired shape.

The polyurethane compositions, in addition to exhibiting excellent radiopacity, are optically transparent. The term "optically transparent" refers to the property of polyurethane compositions of the invention that allows normal visual observation into or through articles prepared from such compositions. For example, blood or other fluids contained in or flowing through an optically transparent catheter can be observed from outside the catheter under normal illumination.

The following examples further illustrate details for the preparation of the compositions of this invention. The invention, which is set forth in the foregoing disclosure, is not to be limited either in spirit or scope by these examples. Those skilled in the art will readily understand that known variations of the conditions and processes of the following preparative procedures can be used to prepare these compositions. Unless otherwise noted, all temperatures are degrees Celsius and all percentages are percentages by weight.

EXAMPLES

Starting materials:

Isocynate—dicyclohexylmethane-4,4′-diisocyanate (available as DESMODUR W from Miles Inc.)

Polyol A—polytetramethylene glycol having a molecular weight of 2000 (available as POLYMEG 2000 from QO Chemicals)

Polyol B—polytetramethylene glycol having a molecular weight of about 3000 (available as TERATHANE 2900 from Du Pont)

Polyol C—polyoxyethylene glycol having a molecular weight of about 3350 (available as PEG 3350 from Union Carbide)

Extender A′—dibromoneopentyl glycol (available as FR-522 from Ameribrom, Inc.)

Extender B′—tetrabromodipentaerythritol (available as FR-1034 from Ameribrom, Inc.)

Extender C′—bis(2-hydroxyethyl ether) of tetrabromobisphenol A (available as BA-50P from Great Lakes Chemical Corporation)

Extender D′—diethylene glycol

Catalyst—dibutyltin dilaurate (available as DABCO T-12 from Air Products and Chemicals, Inc.)

Antioxidant—tetrakis[methylene(3,5-di-tert-butyl-4-hydroxycinnamate)]methane (available as IRGONOX 1010 from Ciba-Geigy)

Processing aid—N,N-dioleoylethylenediamine (available as GLYCOLUBE VL from Lonza)

General Procedure:

Each example was carried out using 0.05 wt. % catalyst, 0.1 wt. % antioxidant, and 0.15 wt. % processing aid based on the total reaction mixture. Proportions of the reactive isocyanate, polyol, and extender components (given as equivalent ratios relative to the isocyanate), as well as hard segment and bromine content of the resultant polyurethanes, are listed in Table 1.

TABLE 1

Compositions used for polyurethanes of the invention

| Example | Polyol Identity | Polyol Equiv. ratio[1] | Extender Identity | Extender Equiv. ratio[2] | Relative ratio[3] | Hard Segment (wt. %) | Bromine (wt. %) |
| --- | --- | --- | --- | --- | --- | --- | --- |
| 1 | A | 0.11 | A′<br>B′ | 0.775<br>0.095 | 89:11 | 70.0 | 21.07 |
| 2 | A | 0.10 | A′<br>C′ | 0.79<br>0.089 | 90:10 | 71.5 | 21.05 |
| 3 | A<br>B | 0.054<br>0.026 | A′ | 0.9 | — | 72.8 | 21.06 |
| 4 | A | 0.08 | A′<br>D′ | 0.857<br>0.043 | 95:5 | 75.4 | 21.06 |
| 5 | A | 0.116 | A′<br>B′ | 0.74<br>0.124 | 86:14 | 69.1 | 21.05 |
| 6 | A | 0.145 | A′<br>B′ | 0.572<br>0.263 | 69:31 | 65.3 | 21.07 |
| 7 | A<br>C | 0.1<br>0.007 | A′<br>B′ | 0.783<br>0.097 | 89:11 | 69.7 | 21.09 |
| 8 | B | 0.079 | A′ | 0.802 | 89:11 | 68.7 | 21.04 |

TABLE 1-continued

Compositions used for polyurethanes of the invention

| Example | Polyol Identity | Equiv. ratio[1] | Extender Identity | Equiv. ratio[2] | Relative ratio[3] | Hard Segment (wt. %) | Bromine (wt. %) |
|---|---|---|---|---|---|---|---|
| | | | B | 0.099 | | | |

[1] Equivalent ratio of polyol to isocyanate
[2] Equivalent ratio of extender to isocyanate
[3] Relative ratio of extender A to the other extender The polyether polyols, bromine-containing chain extenders, antioxidant, and processing aid were mixed in a stainless steel reactor, which was then placed in a convection oven at a temperature of about 100°–110° C. until a molten liquid mixture was obtained (typically about 3–4 hours). The isocyanate and catalyst were added to a dry container and warmed in an oven at about 60° C. until used.

The molten polyol component was then vigorously stirred with a high speed homogenizer and maintained at a temperature of about 100° C. The isocyanate component was then added in one portion to the reactor. The resultant mixture was stirred for about 15–20 seconds, after which it was poured into a teflon-lined tray and post-cured in an infrared oven for five minutes at 120° C. and an additional five minutes at 90° C. The molded material was removed from the oven and allowed to cool to room temperature.

The resultant white opaque slab was granulated and dried in a vacuum oven at a temperature below 66° C. for about 16 hours. The dried granulate was then processed using a single-screw extruder at temperatures of from 93°–232° C. to give optically transparent strands of polyurethane product. The temperatures used for extrusion of the Examples are listed in Table 2. The strands were then pelletized. The pelletized polyurethane was injection molded at about the same temperatures as used for the extrusions to form plaques having a thickness of ⅛ inch (about 3.2 mm). Physical properties of the polyurethane plaques are listed in Table 3.

TABLE 2

Extrusion temperatures

| Example | Extrusion temperature (°C.) |
|---|---|
| 1 | 138 |
| 2 | 138 |
| 3 | 138 |
| 4 | 154 |
| 5 | 138–149 |
| 6 | 138–149 |
| 7 | 132–143 |
| 8 | 132–143 |

TABLE 3

Physical properties of polyurethanes plaques of the invention

| | Example | | | | | | | |
|---|---|---|---|---|---|---|---|---|
| | 1 | 2 | 3 | 4 | 5 | 6 | 7 | 8 |
| Elongation (MPa) | 2.41 | 2.41 | 2.46 | 1.43 | 2.55 | 3.03 | 1.83 | 2.57 |
| Tensile strength (break) (MPa) | 27.2 | 31.3 | 28.8 | 35.8 | 24.4 | 17.2 | 25.4 | 20.5 |
| Modulus (MPa) | | | | | | | | |
| At 100% | 21.0 | 21.8 | 24.0 | 27.6 | 17.2 | 14.0 | 17.1 | 19.4 |
| At 200% | 23.1 | 22.7 | 24.5 | 28.2 | 17.8 | 15.8 | 17.0 | 20.0 |
| At 300% | 25.2 | 24.6 | 26.2 | — | 20.4 | 18.8 | — | 20.8 |
| Flex modulus (MPa) | | | | | | | | |
| Dry | 273.2 | 1078.0 | 1033.7 | 1285.6 | 738.4 | 401.8 | 610.7 | 596.3 |
| Wet (24 hrs) | 156.7 | 693.0 | 662.2 | 916.0 | 226.7 | 968.9 | 280.6 | 333.1 |
| Shore D hardness | 70 | 70 | 70 | 74 | 66 | 62 | 68 | 65 |

What is claimed is:

1. A radiopaque polyurethane composition comprising a reaction product of
   (a) a cycloaliphatic diisocyanate;
   (b) at least one polyether diol having a molecular weight of from 500 to 6000;
   (c) isocyanate-reactive bromine-containing compound selected from the group consisting of
      (i) tetrabromodipentaerythritol and
      (ii) a mixture of tetrabromodipentaerythritol and dibromoneopentyl glycol; and
   (d) optionally, a catalyst;
   wherein the amount of component (c) is such that the amount of bromine in the polyurethane composition is at least 15% by weight,
   wherein the weight ratio of component (b) to component (c) is from 2:98 to 55:45, and
   wherein the components are reacted at an isocyanate index of from 0.95 to 1.2.

2. A radiopaque polyurethane composition according to claim 1 wherein the cycloaliphatic diisocyanate is dicyclohexylmethane-4,4'-diisocyanate.

3. A radiopaque polyurethane composition according to claim 1 wherein the amount of bromine in the polyurethane composition is 20 to 30% by weight.

4. A radiopaque polyurethane composition according to claim 1 wherein the weight ratio of component (b) to component (c) is from 10:90 to 40:60.

5. A radiopaque polyurethane composition according to claim 1 which is optically transparent.

* * * * *